United States Patent
Liu et al.

(10) Patent No.: US 9,494,502 B2
(45) Date of Patent: *Nov. 15, 2016

(54) ROCK TESTING DEVICE WITH THREE-JAW CHUCK FOR DIRECT TENSILE TEST

(71) Applicant: Sichuan University, Chengdu (CN)

(72) Inventors: Jianfeng Liu, Chengdu (CN); Heping Xie, Chengdu (CN); Yang Ju, Chengdu (CN); Jianliang Pei, Chengdu (CN); Lu Wang, Chengdu (CN); Huining Xu, Chengdu (CN); Fei Wu, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,082

(22) Filed: Feb. 3, 2016

(65) Prior Publication Data

US 2016/0231213 A1    Aug. 11, 2016

(30) Foreign Application Priority Data

Feb. 9, 2015  (CN) .......................... 2015 1 0068203

(51) Int. Cl.
*G01N 3/08* (2006.01)
(52) U.S. Cl.
CPC ...................... *G01N 3/08* (2013.01)
(58) Field of Classification Search
CPC ............. G01N 3/08; G01N 3/00; G01L 3/24
USPC .................. 73/826, 788, 796, 806, 760, 862
See application file for complete search history.

(56) References Cited

U.S. PATENT DOCUMENTS

| | | | | |
|---|---|---|---|---|
| 2008/0276719 | A1* | 11/2008 | Xu | G01N 3/08 73/831 |
| 2009/0266548 | A1* | 10/2009 | Olsen | E21B 49/006 166/308.1 |
| 2014/0357461 | A1* | 12/2014 | Yokoyama | E21D 9/087 483/1 |

* cited by examiner

*Primary Examiner* — Lisa Caputo
*Assistant Examiner* — Nigel Plumb
(74) *Attorney, Agent, or Firm* — Matthias Scholl, PC; Matthias Scholl (57) ABSTRACT

A device for fixing a rock sample, the device including: a lower clamp and an upper clamp. The lower clamp includes: a lower connector connected to a bottom loading base, a lower end cap for fixing samples, a lower chain connecting the lower connector and the lower end cap, a first spiral spring, a first central position-limit mechanism, and a second central position-limit mechanism. The lower end cap includes: a first sample fixing groove and a first connecting segment. The upper clamp includes: an upper connector connected to a top loading base, an upper end cap for fixing the samples, an upper chain connecting with the upper connector and the upper end cap, a second spiral spring, a third central position-limit mechanism, and a fourth central position-limit mechanism. The upper end cap includes a second sample fixing groove and a second connecting segment.

3 Claims, 6 Drawing Sheets

ROCK TESTING DEVICE WITH THREE-JAW CHUCK FOR DIRECT TENSILE TEST

CROSS-REFERENCE TO RELATED APPLICATIONS

Pursuant to 35 U.S.C. §119 and the Paris Convention Treaty, this application claims the benefit of Chinese Patent Application No. 201510068203.9 filed Feb. 9, 2015, the contents of which are incorporated herein by reference. Inquiries from the public to applicants or assignees concerning this document or the related applications should be directed to: Matthias Scholl PC., Attn.: Dr. Matthias Scholl Esq., 245 First Street, 18th Floor, Cambridge, Mass. 02142.

BACKGROUND OF THE INVENTION

Field of the Invention

The invention relates to a device for conducting direct tensile test on fragile materials, and more particularly to a device for fixing a rock sample.

Description of the Related Art

Direct tensile test is typically adopted for testing tensile strength of rock samples. However, because the fixing device for fixing the rock samples has structural limits, the test results are often inaccurate and the rock samples are easily damaged during the test.

SUMMARY OF THE INVENTION

In view of the above-described problems, it is one objective of the invention to provide a device for fixing a rock sample that ensures the coincidence between the center line of the spiral spring and the center line of the testing machine and the consistence in the loading rigidity at two ends of the test sample, thus improving the accuracy of the test result and effectively testing the mechanical effect after the peak stress.

To achieve the above objective, in accordance with one embodiment of the invention, there is provided a device for fixing the rock sample. The device comprises: a lower clamp and an upper clamp. The lower clamp comprises: a lower connector connected to a bottom loading base of a testing machine, a lower end cap for fixing samples, a lower chain connecting the lower connector and the lower end cap, a first spiral spring, a first central position-limit mechanism, and a second central position-limit mechanism. The lower end cap comprises: a first sample fixing groove and a first connecting segment. The upper clamp comprises: an upper connector connected to a top loading base of the testing machine, an upper end cap for fixing the samples, an upper chain connecting with the upper connector and the upper end cap, a second spiral spring, a third central position-limit mechanism, and a fourth central position-limit mechanism. The upper end cap comprises: a second sample fixing groove and a second connecting segment.

The first central position-limit mechanism, the second central position-limit mechanism, the third central position-limit mechanism, and the fourth central position-limit mechanism have the same structure and each central position-limit mechanism comprises: a scroll chuck, supports, and a connecting plate. One end of each of the supports is connected to the connecting plate, and the other end of each of the supports is connected to the scroll chuck.

The first central position-limit mechanism and the bottom loading base of the testing machine are assembled. A first scroll chuck in the first central position-limit mechanism contacts the bottom loading base of the testing machine, and the lower connector is disposed in a center hole of the first scroll chuck. A free end of each of the three claws of the first scroll chuck in the first central position-limit mechanism contacts an external side of the lower connector. The second central position-limit mechanism and the lower end cap are assembled. A second scroll chuck in the second central position-limit mechanism contacts an outer bottom wall of the first sample fixing groove of the lower end cap, and the first connecting segment of the lower end cap is disposed in a center hole of the second scroll chuck. A free end of each of the three claws of the second scroll chuck in the second central position-limit mechanism contacts an external side of the first connecting segment of the lower end cap. One end of the first spiral spring is connected to the connecting plate of the first central position-limit mechanism, and the other end of the first spiral spring is connected to the connecting plate of the second central position-limit mechanism. The lower chain is disposed in a space enclosed by the first central position-limit mechanism, the first spiral spring, and the second central position-limit mechanism.

The third central position-limit mechanism and the upper end cap are assembled. A third scroll chuck in the third central position-limit mechanism contacts an outer bottom wall of the second sample fixing groove of the upper end cap, and the second connecting segment of the upper end cap is disposed in a center hole of the third scroll chuck. A free end of each of the three claws of the third scroll chuck in the third central position-limit mechanism contact an external side of the second connecting segment of the upper end cap. The fourth central position-limit mechanism and the top loading base of the testing machine are assembled. A fourth scroll chuck in the fourth central position-limit mechanism contacts the top loading base of the testing machine, and the upper connector is disposed in a center hole of the fourth scroll chuck. A free end of each of the three claws of the fourth scroll chuck in the fourth central position-limit mechanism contacts an outer side of the upper connector. One end of the second spiral spring is connected to the connecting plate of the third central position-limit mechanism, and the other end of the second spiral spring is connected to the connecting plate of the fourth central position-limit mechanism. The upper chain is disposed in a space enclosed by the third central position-limit mechanism, the second spiral spring, and the fourth central position-limit mechanism.

In a class of this embodiment, in the first central position-limit mechanism, the second central position-limit mechanism, the third central position-limit mechanism, and the fourth central position-limit mechanism, the supports are four round rods; the connecting plate is a circular plate; the four round rods are uniformly mounted between each of the scroll chucks and a circular surface of each of the connecting plates. Or, the supports are two boards having a circular-arc cross section; the connecting plate is a circular plate; the two boards are symmetrically mounted between each of the scroll chucks and a circular surface of each of the connecting plates.

In a class of this embodiment, the scroll chucks are manual chucks, pneumatic chucks, or hydraulic chucks.

Advantages of the device for fixing the rock sample according to embodiments of the invention are summarized as follows:

1. Because each of the lower clamp and the upper clamp is provided with the spiral spring and two central position-limit mechanisms, the loading rigidity at both ends of the rock sample during the test are consistent, and the mechanical effect after a peak stress of the rock can be tested more effectively. In addition, the center line of the spiral spring and the center line of the testing machine coincide in the test due to the scroll chucks in the central position-limit mechanisms of the lower clamp and the upper clamp. Thus, the occurrence of additional eccentric force is avoided, and the success rate of the test as well as the accuracy of the test result is improved.

2. Since the supports in the first central position-limit mechanism, the second central position-limit mechanism, the third central position-limit mechanism, and the fourth central position-limit mechanism are four round rods or two boards having the circular-arc cross section, the bolts can be easily inserted when connecting the chains and the end caps. Thus, the operation is much simple and convenient, and the test efficiency is improved.

BRIEF DESCRIPTION OF THE DRAWINGS

The invention is described hereinbelow with reference to the accompanying drawings, in which.

In the drawings; the following reference numbers are used: 1. Bottom loading base of a testing machine; 2. Scroll chuck; 2-1. First jaw chuck; 2-2. Second jaw chuck; 2-3. Claw; 2-4. First bevel gear; 2-5. Second bevel gear; 2-5-1. Plane threads; 2-5-2. Bevel teeth; 3. Lower connector; 4. Support; 5. Connecting plate; 6. Lower chain; 7. Lower bolt; 8. Lower end cap; 9. Rock sample; 10. Upper end cap; 11. Upper bolt; 12. Upper chain; 13. Upper connecter; 14. Top loading base of a testing machine; 15. First spiral spring; 16. Second spiral spring; 100. First central position-limit mechanism; 200. Second central position-limit mechanism; 300. Third central position-limit mechanism; and 400. Fourth central position-limit mechanism.

DETAILED DESCRIPTION OF THE EMBODIMENTS

For further illustrating the invention, experiments detailing a device for fixing a rock sample in a direct tension test based on scroll chucks are described below. It should be noted that the following examples are intended to describe and not to limit the invention.

Figure 1:
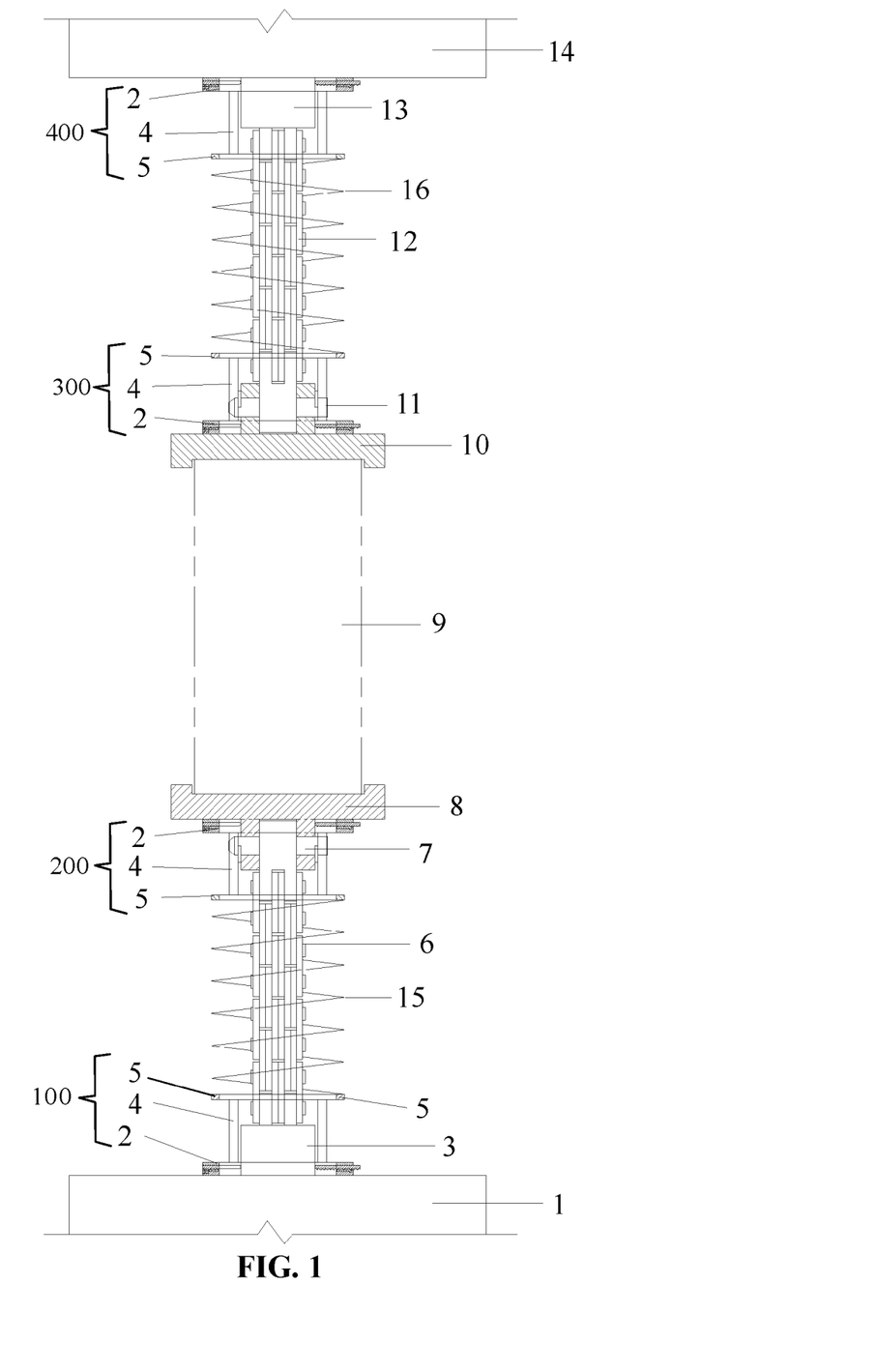
FIG. 1 is a structure diagram of a device for fixing a rock sample in accordance with one embodiment of the invention.

The device for fixing the rock sample comprises: a lower clamp and an upper clamp as shown in the FIG. 1. The lower clamp comprises: a lower connector 3 connected to a bottom loading base 1 of a testing machine, a lower end cap 8 for fixing samples, a lower chain 6 connecting the lower connector and the lower end cap, a first spiral spring 15, a first central position-limit mechanism 100, and a second central position-limit mechanism 200. The lower end cap 8 comprises: a first sample fixing groove and a first connecting segment. The first spiral spring 15 is a cylindrical spiral compression spring. The upper clamp comprises: an upper connector 13 connected to a top loading base 14 of the testing machine, an upper end cap 10 for fixing the samples, an upper chain 12 connecting with the upper connector and the upper end cap, a second spiral spring 16, a third central position-limit mechanism 300, and a fourth central position-limit mechanism 400. The upper end cap 10 comprises: a second sample fixing groove and a second connecting segment. The second spiral spring 16 is the cylindrical spiral compression spring.

Figure 2:
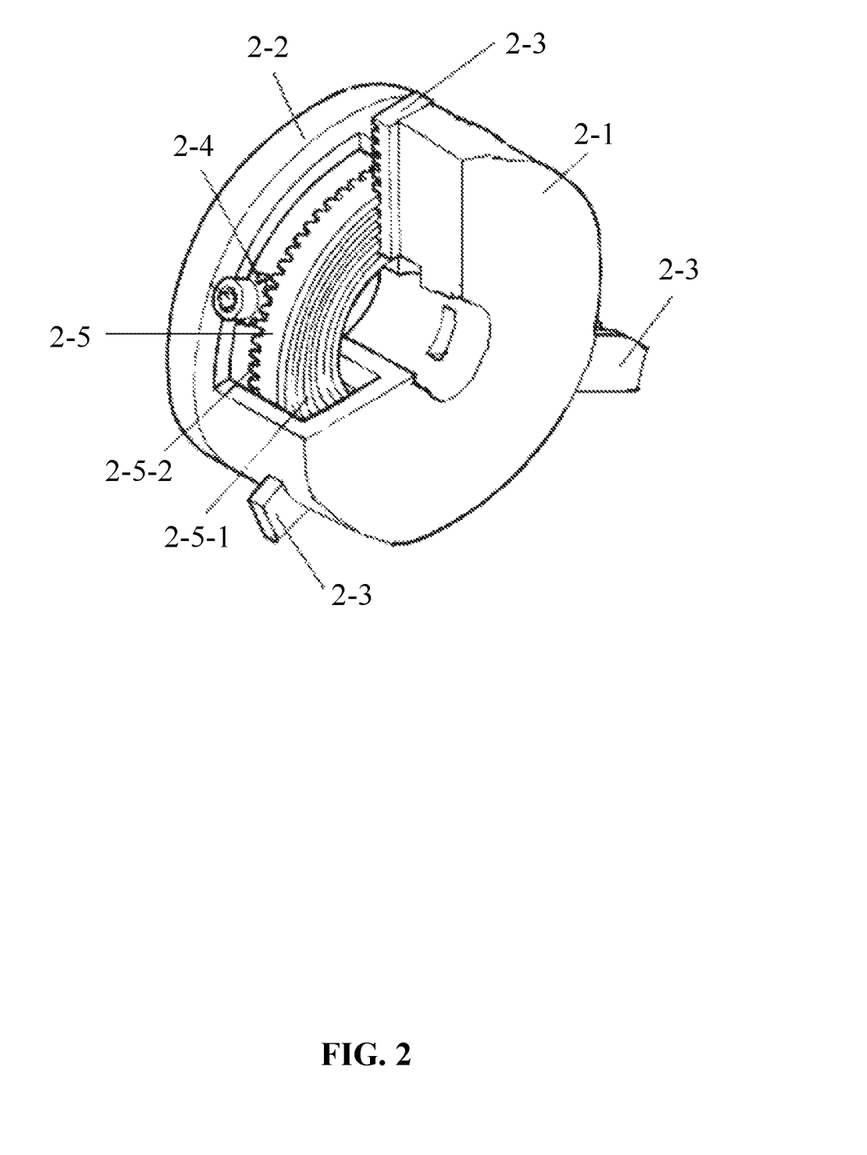
FIG. 2 is a structure diagram of a scroll chuck in accordance with one embodiment of the invention.
Figure 3:
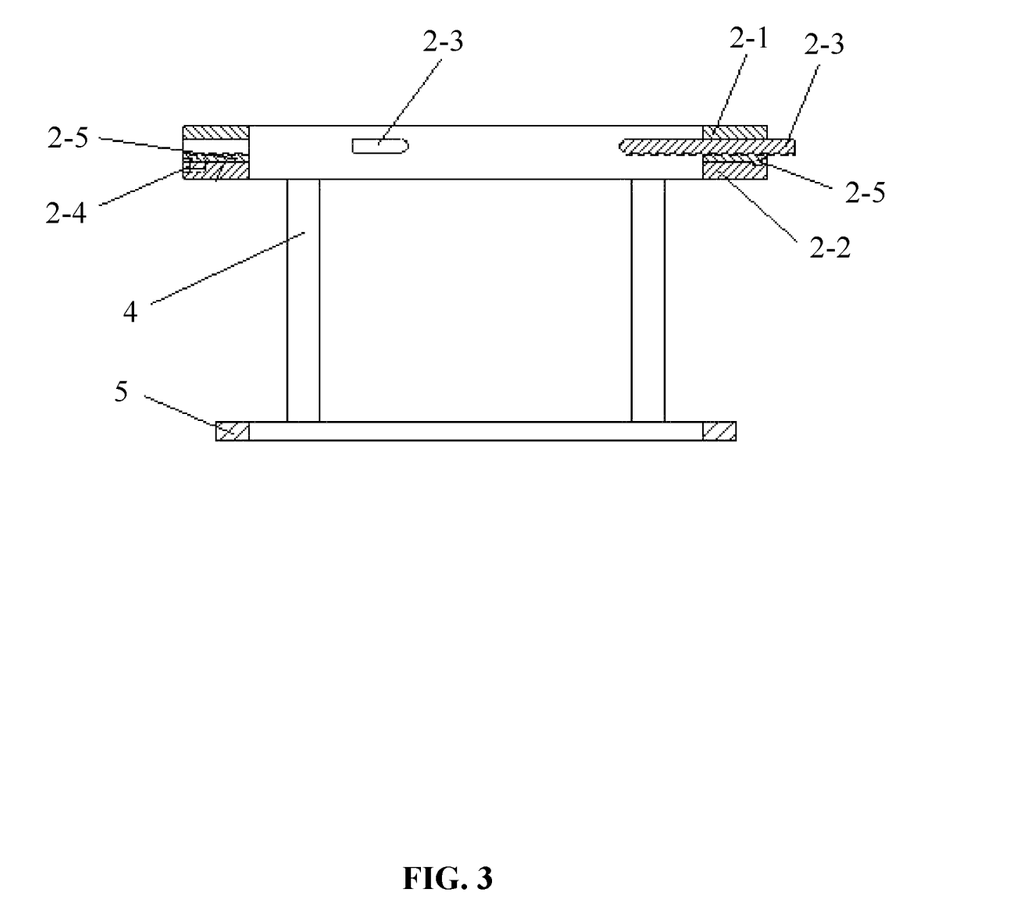
FIG. 3 is a structure diagram of a first central position-limit mechanism, a second central position-limit mechanism, a third central position-limit mechanism, or a fourth central position-limit mechanism in a device for fixing a rock sample (the supports are round rods) in accordance with one embodiment of the invention.
Figure 4:
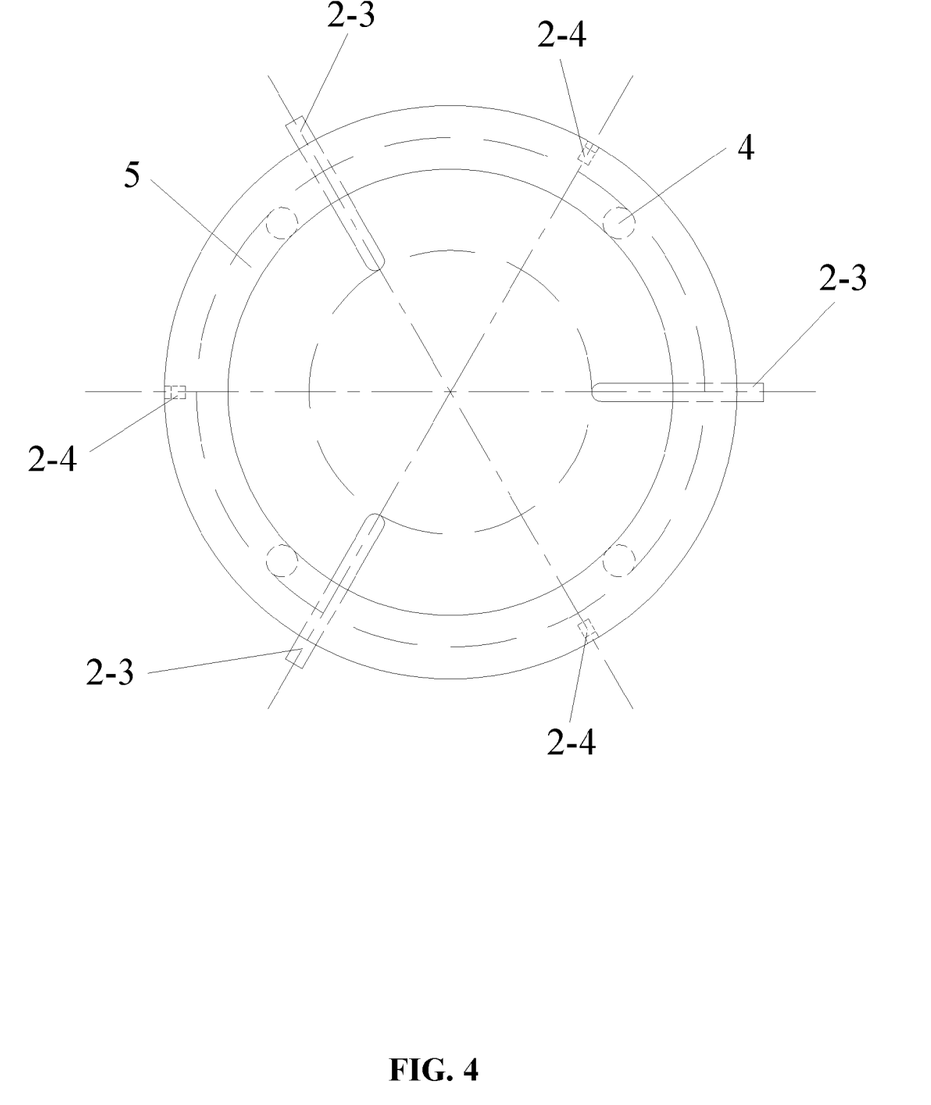
FIG. 4 is a top view of the FIG. 3.

The first central position-limit mechanism 100, the second central position-limit mechanism 200, the third central position-limit mechanism 300, and the fourth central position-limit mechanism 400 have the same structure and each central position-limit mechanism comprises: a scroll chuck 2, supports 4, and a connecting plate 5, as shown in FIGS. 3 and 4. The scroll chucks are manual chucks having a structure shown in FIG. 2. Each scroll chuck 2 comprises: a first jaw chuck 2-1, a second jaw chuck 2-2, three claws 2-3, a first bevel gear 2-4, and a second bevel gear 2-5. The first jaw chuck 2-1 and the second jaw chuck 2-2 are circular chucks and center holes of both the first jaw chuck 2-1 and the second jaw chuck 2-2 have the same diameter. One side of the second bevel gear 2-5 is provided with bevel teeth 2-5-2 engaging with the first bevel gear, and the other side of the second bevel gear 2-5 is provided with plane threads 2-5-1. Threads matching the plane threads 2-5-1 are disposed on the three claws 2-3. After assembly, the first bevel gear 2-4 and the second bevel gear 2-5 are disposed in a space enclosed by the first jaw chuck 2-1 and the second jaw chuck 2-2. The three claws 2-3 are respectively disposed in three guide grooves which are distributed with an angle of 120° in the first claw chuck 2-1; and the threads of the claws engage with the plane threads 2-5-1 of the second bevel gear. The supports 4 are four round rods. The connecting plate 5 is a circular plate, and a diameter of a center hole of the connecting plate 5 is equivalent to the diameters of the center holes of both the first jaw chuck 2-1 and the second jaw chuck 2-2. The four round rods are uniformly mounted between the second jaw chuck 2-2 and a circular surface of the connecting plate 5. One end of each of the round rods is connected to the connecting plate 5, and the other end of each of the round rods is connected to the second jaw chuck 2-2 of each scroll chuck.

Members or components of the lower clamp are assembled as follows: the first central position-limit mechanism 100 and the bottom loading base 1 of the testing machine are assembled. The first jaw chuck 2-1 of the first scroll chuck in the first central position-limit mechanism 100 contacts the bottom loading base 1 of the testing machine. The lower connector 3 is disposed in the center holes of the first jaw chuck 2-1 and the second jaw chuck 2-2. A free end of each of the three claws of the first scroll chuck in the first central position-limit mechanism 100 contacts an external side of the lower connector 3. The second central position-limit mechanism 200 and the lower end cap 8 are assembled. The first jaw chuck 2-1 of a second scroll chuck in the second central position-limit mechanism 200 contacts an outer bottom wall of the first sample fixing groove of the lower end cap 8. The first connecting segment of the lower end cap 8 is disposed in the center holes of the first jaw chuck 2-1 and the second jaw chuck 2-2. A free end of each of the three claws of the second scroll chuck in the second central position-limit mechanism 200 contacts an external side of the first connecting segment of the lower end cap. One end of the first spiral spring 15 is connected to the connecting plate 5 of the first central position-limit mechanism 100, and the other end of the first spiral spring 15 is connected to the connecting plate 5 of the second central position-limit mechanism 200. A lower end of the lower chain 6 is connected to the lower connector 3 disposed on the bottom loading base 1 of the testing machine; and a dismountable connection between the upper end of the lower chain and the lower end cap is formed by a lower bolt 7. The lower chain 6 is disposed in a space enclosed by the first central position-limit mechanism 100, the first spiral spring 15, and the second central position-limit mechanism 200.

Members or components of the upper clamp are assembled as follows: the third central position-limit mechanism 300 and the upper end cap 10 are assembled. The first jaw chuck 2-1 of the third scroll chuck in the third central position-limit mechanism 300 contacts an outer bottom wall of the second sample fixing groove of the upper end cap 10. The second connecting segment of the upper end cap 10 is disposed in the center holes of the first jaw chuck 2-1 and the second jaw chuck 2-2. A free end of each of the three claws of the third scroll chuck in the third central position-limit mechanism 300 contact an external side of the second connecting segment of the upper end cap. The fourth central position-limit mechanism 400 and the top loading base 14 of the testing machine are assembled. The first jaw chuck 2-1 of the fourth scroll chuck in the fourth central position-limit mechanism 400 contacts the top loading base 14 of the testing machine. The upper connector 13 is disposed in the center holes of the first jaw chuck 2-1 and the second jaw chuck 2-2. A free end of each of the three claws of the fourth scroll chuck in the fourth central position-limit mechanism 400 contacts an outer side of the upper connector 13. One end of the second spiral spring 16 is connected to the connecting plate 5 of the third central position-limit mechanism 300, and the other end of the second spiral spring 16 is connected to the connecting plate 5 of the fourth central position-limit mechanism 400. An upper end of the upper chain 12 is connected to the upper connector 13 disposed on the top loading base 14 of the testing machine; and a dismountable connection between the lower end of the upper chain and the upper end cap is formed by an upper bolt 11. The upper chain 12 is disposed in a space enclosed by the third central position-limit mechanism 300, the second spiral spring 16, and the fourth central position-limit mechanism 400.

The mode for mounting the rock sample 9 is shown in the FIG. 1. Both ends of the rock sample are adhered with the first sample fixing groove of the lower end cap 8 and the second sample fixing groove of the upper end cap 10 by a high-strength adhesive.

Figure 5:
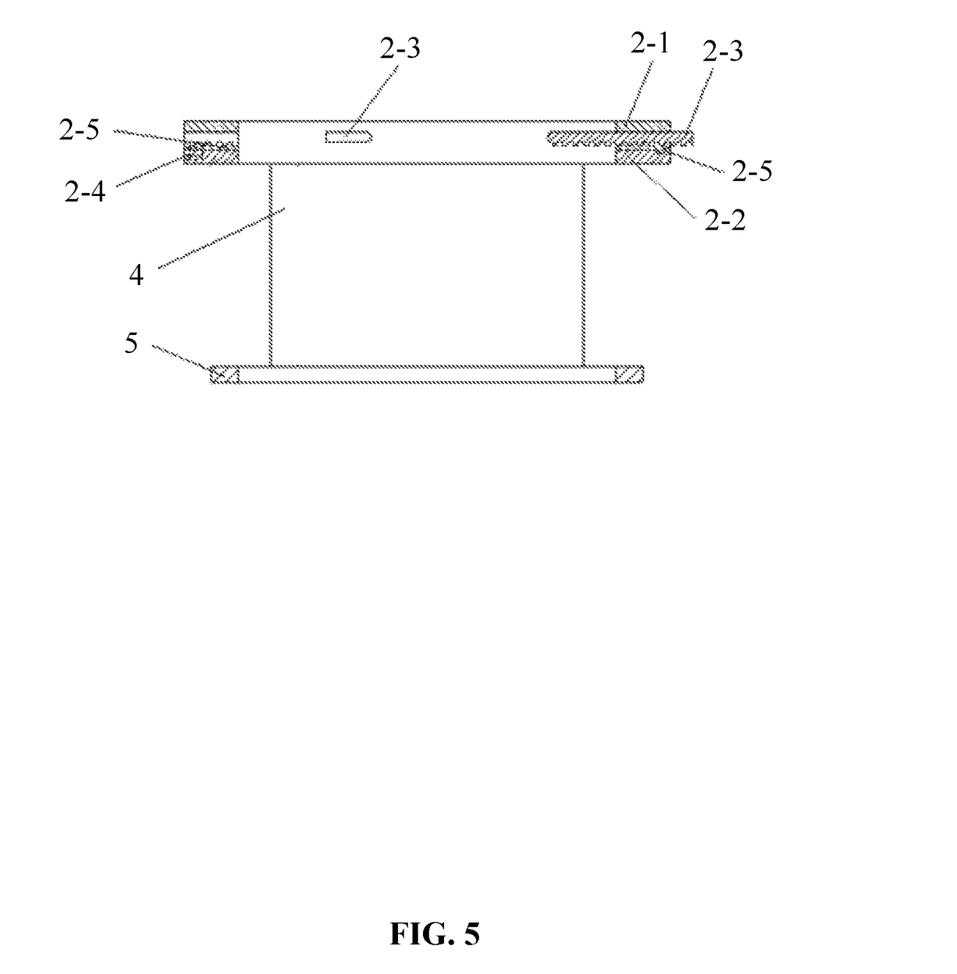
FIG. 5 is a structure diagram of a first central position-limit mechanism, a second central position-limit mechanism, a third central position-limit mechanism, or a fourth central position-limit mechanism in a device for fixing a rock sample (the supports are boards having a circular-arc cross section) in accordance with one embodiment of the invention.
Figure 6:
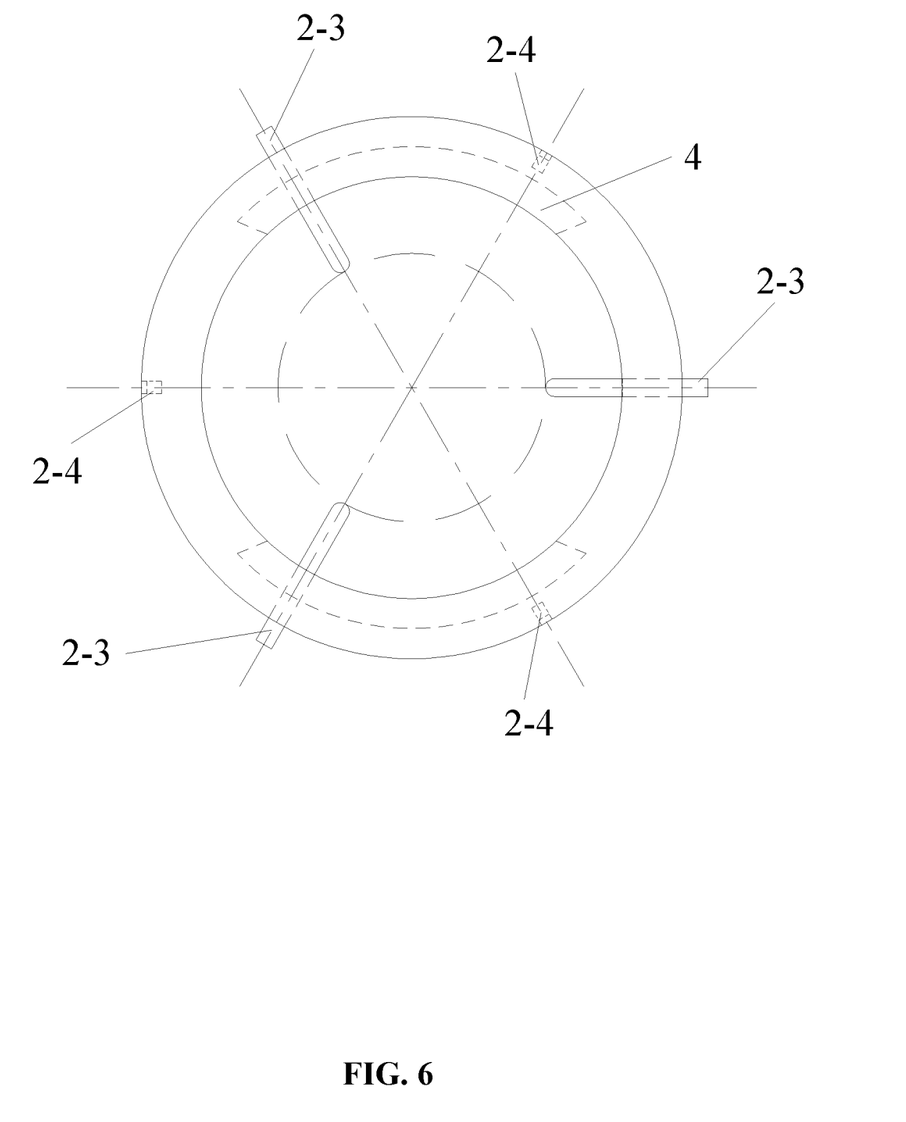
FIG. 6 is a top view of the FIG. 5.

The invention is not limited to the above embodiments. For example, the first central position-limit mechanism 100, the second central position-limit mechanism 200, the third central position-limit mechanism 300, and the fourth central position-limit mechanism 400 can also have the structure shown in FIGS. 5 and 6. That is, the supports 4 are two boards having a circular-arc cross section; the connecting plate 5 is the circular plate; the two boards are symmetrically mounted between the second jaw chuck 2-2 and the circular surface of the connecting plate 5. One end of each of the two boards is connected to the connecting plate 5, and the other end of each of the two boards is connected to the second jaw chuck 2-2. The scroll chucks are pneumatic chucks or hydraulic chucks.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for fixing a rock sample, the device comprising:
   a) a lower clamp, the lower clamp comprising: a lower connector connected to a bottom loading base of a testing machine, a lower end cap for fixing samples, a lower chain connecting the lower connector and the lower end cap, a first spiral spring, a first central position-limit mechanism, and a second central position-limit mechanism; the lower end cap comprising: a first sample fixing groove and a first connecting segment;
   b) an upper clamp, the upper clamp comprising: an upper connector connected to a top loading base of the testing machine, an upper end cap for fixing the samples, an upper chain connecting with the upper connector and the upper end cap, a second spiral spring, a third central position-limit mechanism, and a fourth central position-limit mechanism; the upper end cap comprising: a second sample fixing groove and a second connecting segment;
   wherein
      the first central position-limit mechanism, the second central position-limit mechanism, the third central position-limit mechanism, and the fourth central position-limit mechanism have the same structure and each central position-limit mechanism comprises: a scroll chuck, supports, and a connecting plate; one end of each of the supports is connected to the connecting plate, and the other end of each of the supports is connected to the scroll chuck;
      the first central position-limit mechanism and the bottom loading base of the testing machine are assembled; a first scroll chuck in the first central position-limit mechanism contacts the bottom loading base of the testing machine, and the lower connector is disposed in a center hole of the first scroll chuck; a free end of each of the three claws of the first scroll chuck in the first central position-limit mechanism contacts an external side of the lower connector; the second central position-limit mechanism and the lower end cap are assembled; a second scroll chuck in the second central position-limit mechanism contacts an outer bottom wall of the first sample fixing groove of the lower end cap, and the first connecting segment of the lower end cap is disposed in a center hole of the second scroll chuck; a free end of each of the three claws of the second scroll chuck in the second central position-limit mechanism contacts an external side of the first connecting segment of the lower end cap; one end of the first spiral spring is connected to the connecting plate of the first central position-limit mechanism, and the other end of the first spiral spring is connected to the connecting plate of the second central position-limit mechanism; and the lower chain is disposed in a space enclosed by the first central position-limit mechanism, the first spiral spring, and the second central position-limit mechanism; and the third central position-limit mechanism and the upper end cap are assembled; a third scroll chuck in the third central position-limit mechanism contacts an outer bottom wall of the second sample fixing groove of the upper end cap, and the second connecting segment of the upper end cap is disposed in a center hole of the third scroll chuck; a free end of each of the three claws of the third scroll chuck in the third central position-limit mechanism contact an external side of the second connecting segment of the upper end cap; the fourth central position-limit mechanism and the top loading base of the testing machine are assembled; a fourth scroll chuck in the fourth central position-limit mechanism contacts the top loading base of the testing machine, and the upper connector is disposed in a center hole of the fourth scroll chuck; a free end of each of the three claws of the fourth scroll chuck in the fourth central position-limit mechanism contacts an outer side of the upper connector; one end of the second spiral spring is connected to the connecting plate of the third central position-limit mechanism, and the other end of the second spiral spring is connected to the connecting plate of the fourth central position-limit mechanism; and the upper chain is disposed in a space enclosed by the third central position-limit mechanism, the second spiral spring, and the fourth central position-limit mechanism.

2. The device of claim 1, wherein in the first central position-limit mechanism, the second central position-limit mechanism, the third central position-limit mechanism, and the fourth central position-limit mechanism, the supports are four round rods; the connecting plate is a circular plate; the four round rods are uniformly mounted between each of the scroll chucks and a circular surface of each of the connecting plate.

3. The device of claim 1, wherein in the first central position-limit mechanism, the second central position-limit mechanism, the third central position-limit mechanism, and the fourth central position-limit mechanism, the supports are two boards having a circular-arc cross section; the connecting plate is a circular plate; the two boards are symmetrically mounted between each of the scroll chucks and a circular surface of each of the connecting plates.

* * * * *